United States Patent [19]
Bonnet

[11] Patent Number: 5,685,853
[45] Date of Patent: Nov. 11, 1997

[54] INJECTION DEVICE

[75] Inventor: Ludwig Bonnet, Knittlingen, Germany

[73] Assignee: Richard Wolf GmbH, Knittlingen, Germany

[21] Appl. No.: 434,131

[22] Filed: May 2, 1995

[30] Foreign Application Priority Data

Nov. 24, 1994 [DE] Germany .............. 9418834 U

[51] Int. Cl.$^6$ .................................... A61M 5/178
[52] U.S. Cl. ................ 604/164; 600/131; 600/106; 600/156
[58] Field of Search .................. 604/164, 165, 604/167, 173, 256, 264, 280, 36; 600/131, 104–106, 156

[56] References Cited

U.S. PATENT DOCUMENTS

| | | |
|---|---|---|
| 4,237,871 | 12/1980 | Bonnet . |
| 4,461,280 | 7/1984 | Baumagartner ............ 604/164 X |
| 4,653,475 | 3/1987 | Seike et al. ............ 604/165 X |
| 4,756,309 | 7/1988 | Sachse et al. . |
| 4,932,942 | 6/1990 | Maslanka ............ 604/164 |
| 5,169,397 | 12/1992 | Sakashita et al. . |
| 5,209,741 | 5/1993 | Spaeth ............ 604/164 |
| 5,211,650 | 5/1993 | Noda ............ 604/256 X |
| 5,261,889 | 11/1993 | Laine et al. ............ 604/164 |
| 5,312,430 | 5/1994 | Rosenbluth et al. . |
| 5,328,480 | 7/1994 | Melker et al. ............ 604/164 |

FOREIGN PATENT DOCUMENTS

GM78 27 905 2/1979 Germany .
3048761 1A 12/1980 Germany .

*Primary Examiner*—Mark Bockelman
*Attorney, Agent, or Firm*—Panitch Schwarze Jacobs & Nadel, P.C.

[57] ABSTRACT

A device for the injection of substances into human tissue by means of an injection cannula (2.0) is axially adjustable along an endoscope shaft (1.0). The cannula is proximally connected to a coupling (1.8). Allocated to the endoscope shaft (1.0) is a guide tube (1.2) for the injection cannula (2.0), which is inserted into this guide tube (1.2) from the proximal end of the device and is detachably connected with the coupling (1.8). In addition, the unit including the guide tube (1.2) and the injection cannula (2.0) is axially adjustable relative to the endoscope shaft (1.0) by means of a handle (5) that can be operated with one hand.

8 Claims, 2 Drawing Sheets

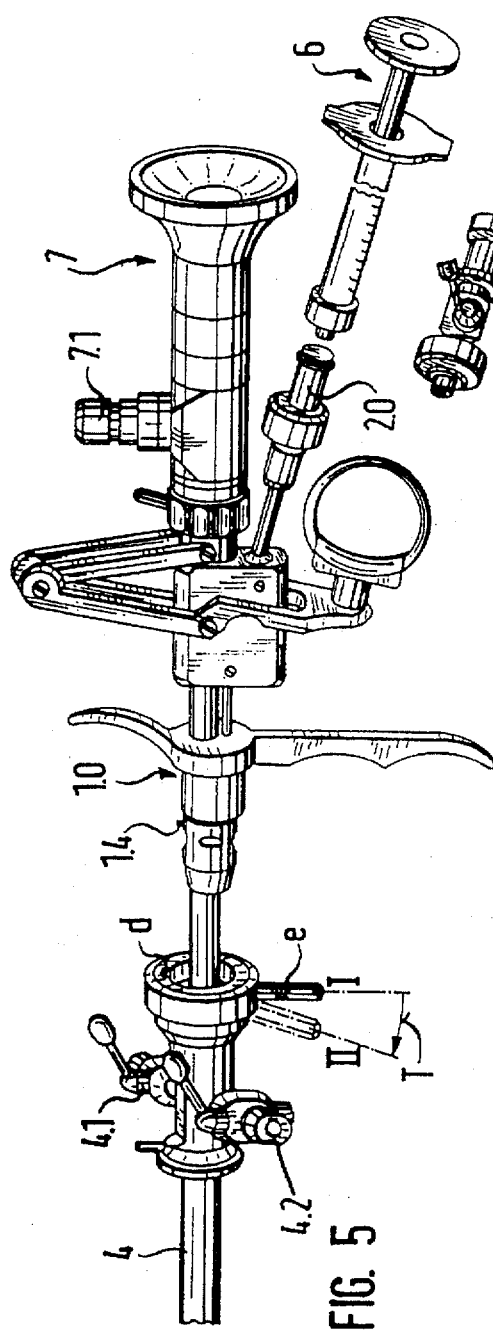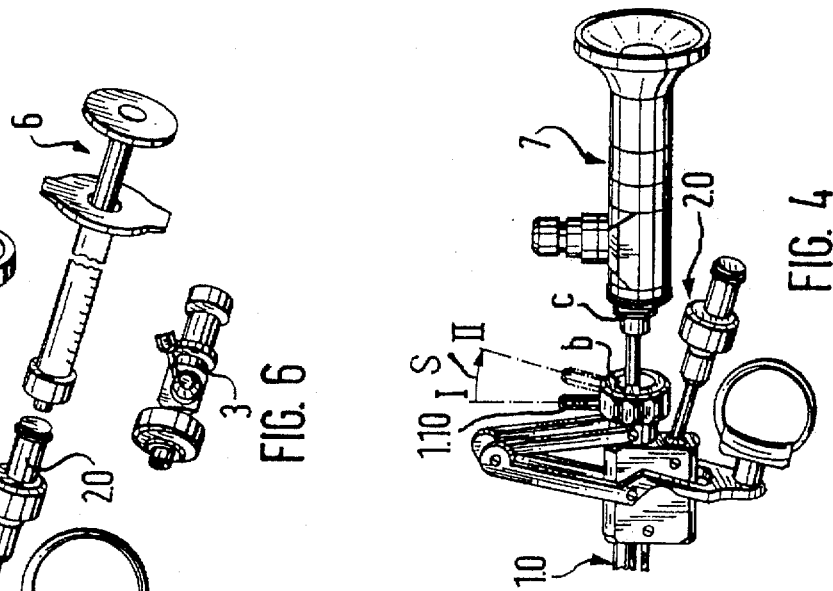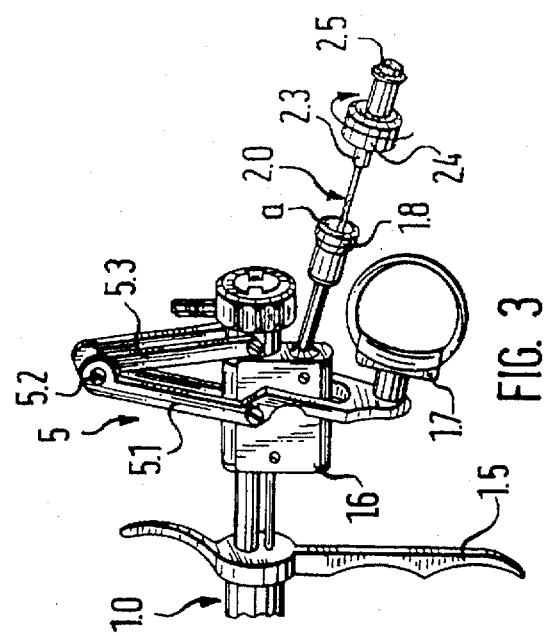

INJECTION DEVICE

FIELD OF THE INVENTION

The present invention pertains to a device for injection of substances into human tissue by means of an injection cannula that is axially adjustable along an endoscope shaft and that is proximally connected to a coupling.

BACKGROUND OF THE INVENTION

Such a device is known from DE-GM 78 27 905, for example. With that device, the effector tube, which is configured as an injection cannula with a distal cannula point, is connected proximally with a cylinder which can be filled with paste, and into the proximal open end of which a piston with an external handle can be screwed. Following the insertion of the distal end of the device into the interior of the body, the injection cannula with the cannula point is displaced distally, out of the shaft that surrounds the endoscope shaft and the injection cannula, and the cannula is stuck into the organ while being observed. Then the paste with which the cylinder was filled is pressed out of the cylinder and through the injection cannula and the cannula point into the organ by means of a screwing down of the piston. Screwed onto the distal end of the injection cannula, which is configured with a relatively large lumen, is a cannula point of a smaller diameter.

At this location, depending on the relative amount of change in cross-section, a significant pressure has to be used by the doctor during the injection. In addition, it is a disadvantage that after usage a relatively large quantity of material that can no longer be recycled remains behind in the injection cannula. This is a disadvantage because such injection substances are relatively expensive, and because problems can arise during cleaning and disinfecting of the injection cannula as a result of dried and adhering injection substances that may be present.

In the case of a hand-held device known from DE-OS 3 048 761 for injection of highly viscous liquids in human medicine, a high-pressure injection pistol is joined to a flexible cannula that can be guided through the working channel of an endoscope. The endoscope and the injection pistol of this known device can only be handled separately from each other, whereby the sticking in of the cannula point that emerges at the distal end of the working channel is carried out by displacement of the flexible cannula, and thus an exactly targeted and sure sticking of the cannula point into the body organ is not possible.

SUMMARY OF THE INVENTION

It is an object of the present invention to make possible a device specifically for the injection of pastes or flowable materials and for the aspiration of body fluids and, for example, of cysts in the urogenital tract, in such a way that the handling of the device for performing the operation can be carried out by one person, that as little material as possible is lost in the device, and that the injection cannula can be specifically adjustable depending on need.

A generic device that achieves this object is characterized, in accordance with the invention, by allocating to the endoscope shaft a guide tube for the injection cannula, which is inserted into the guide tube from the proximal end of the device and is detachably joined with the coupling, and by making the unit comprising the guide tube and the injection cannula axially adjustable relative to the endoscope shaft by means of a handle that can be operated with one hand.

While the device in accordance with the invention is specifically intended for the injection of pastes or flowable substances into human organs and is therefore preferably equipped with an injection cannula as effector tube, it nevertheless allows for the aspiration of body fluids as well. In addition, known flexible or semi-flexible auxiliary instruments such as forceps, catheters, and coagulation electrodes can also be used and guided by the guide tube as effectors, as necessary in place of the injection cannula.

A preferred embodiment of the device in accordance with the invention is created in such a way that the endoscope shaft, the guide tube with the coupling, the effector tube or the injection cannula, and the handle can be jointly supported in or on a proximal block in such a way that the guide tube and the effector tube together with the shaft, can be adjusted axially relative to the endoscope shaft by operating the handle.

An injection cannula used according to the invention as effector tube for the injection of pastes or fluids or even for the aspiration of fluids from body organs has a semi-flexible shaft tube with a cannula point at its distal end and a Luer connection at its proximal end. The size of the injection cannula is so chosen that both aspiration and injection are possible.

The cannula point is configured as thin as possible with a diameter that is, for example, less than 0.9 mm, while the semi-flexible shaft tube, whose inside diameter basically corresponds to the outside diameter of the cannula point, is configured in such a way that, on the one hand, a needle or similar object that has been filled with the material to be injected can be connected to the Luer connection with no additional means and, on the other hand, the material can be pressed through manually, so that at the end of the operation as little material as possible remains in the system.

Following performance of the operation, the entire injection cannula can be easily removed from the guide tube and cleaned or even replaced by a new injection cannula or a different effector tube.

The small wall thickness of the shaft tube of the injection cannula, which is less than 0.2 mm, makes it possible to insert the entire cannula into the cannula guide tube even around curves, on account of its semi-flexible property.

The injection cannula itself can be made with a very small lumen, since sufficient stabilization of the injection cannula is assured as a result of the large-lumen cannula guide tube that is axially guided along the endoscope shaft.

It is advantageous if the cannula point is not screwed onto the injection cannula, but is instead an integral component of same, whereby a jump in the cross-section between the cannula point and the injection cannula can be kept very small.

Of course, for use of effector tubes other than an injection cannula, the coupling at the proximal end of the guide tube can be replaced by an insertion tap of a known design in order to be able to insert and attach flexible auxiliary instruments such as forceps, catheters and coagulation electrodes, as needed.

BRIEF DESCRIPTION OF THE DRAWINGS

The foregoing summary, as well as the following detailed description of a preferred embodiment of the invention, will be better understood when read in conjunction with the appended drawings which show further features and advantages of the invention. For the purpose of illustrating the invention, there is shown in the drawings an embodiment which is presently preferred. It should be understood, however, that the invention is not limited to the precise arrangements and instrumentalities shown. In the drawings:

FIG. 3 shows a perspective view of the proximal part of the device;

FIG. 4 shows the mounting of an endoscope tube with endoscope ocular on the proximal end of the device;

FIG. 5 shows the insertion of the device into a jacket tube or into an external endoscope shaft and the mounting of a Luer syringe to the Luer connector of the injection cannula; and FIG. 6 shows an insertion tap.

DETAILED DESCRIPTION OF PREFERRED EMBODIMENT

Figure 1:
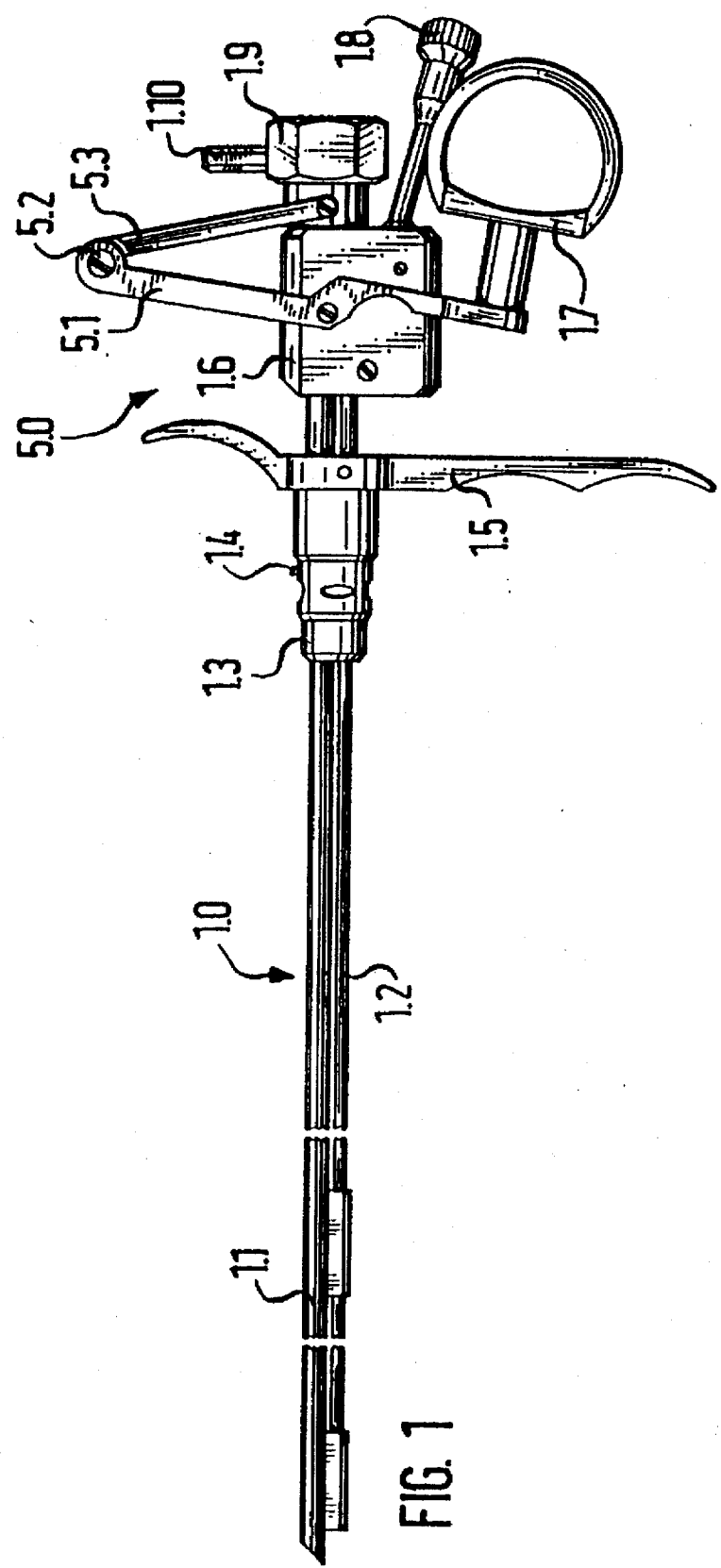
FIG. 1 shows a schematic side view of the device according to the invention.

FIG. 1 shows a preferred embodiment of a working element 1.0 of the device in accordance with the invention, which has an optics guide tube 1.1, hereafter called an endoscope shaft, a cannula guide tube 1.2, a sealing cone 1.3, a positioning pin 1.4, a handle 5 comprising a handgrip 1.5 and a thumb ring 1.7 with a spring link, a movable seating block 1.6, a connection coupling 1.8 for a cannula tube or the like, a clamping ring 1.9 and a toggle clamp 1.10. A jacket tube 4 that sheathes the device on the distal side and is not shown in FIG. 1 will be discussed later with the aid of FIG. 5. The cannula guide tube 1.2, together with the injection cannula 2.0 shown in FIG. 2 and the block 1.6, can be adjusted axially relative to the endoscope shaft 1.1 by means of one-handed operation at the handle 5.

In FIG. 1, these elements are shown in their rest position, whereby a spring link connected to a lever arm of the thumb ring 1.7 forces the block 1.6 together with the cannula guide tube 1.2 into this rest position.

Figure 2:
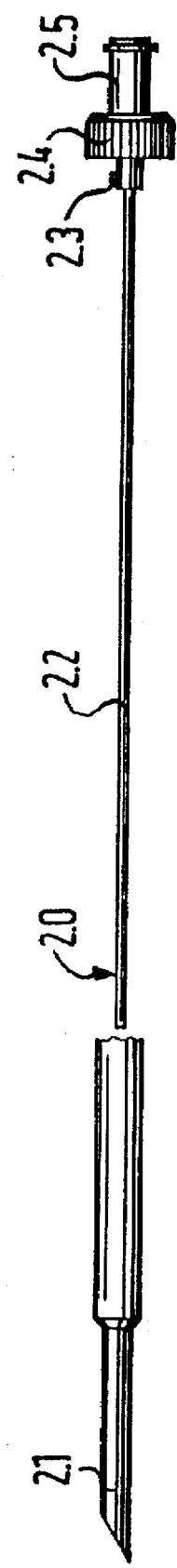
FIG. 2 shows an embodiment of an injection cannula used in conjunction with the device according to FIG. 1.

The injection cannula 2.0 shown in FIG. 2 has at its distal end, which is shown enlarged, a cannula point 2.1, in its middle section, a semi-flexible shaft tube 2.2, and at the proximal end a guide lug for positioning the injection cannula 2.0 in the cannula guide tube 1.2, a union nut 2.4 that can be screwed onto an external thread on the coupling 1.8 of the cannula guide tube 1.2, and a Luer connection 2.5 to which the Luer syringe 6 (FIG. 5) can be connected. Since the proximal end of the cannula guide tube 1.2 emerges from the block 1.6 at an acute angle with respect to the endoscope axis, the parts connected to the cannula connection 1.8, in particular the Luer syringe or a compressed gas connection, are not in the way of the endoscope ocular.

As a result of its play-free guidance by means of the cannula guide tube, the injection cannula can also be made thin in its middle shaft tube section 2.2 and, as a result, has the flexibility necessary for the angled insertion of the injection cannula into the cannula guide tube 1.2 and is stabilized by the latter.

The cannula guide tube 1.2 is configured at its distal end in such a way that it guides the front section of the injection cannula 2.0 in a play-free manner. As a result, good stabilization of the injection cannula 2.0 in the guide tube 1.2 is achieved, so that the cannula point 2.1 remains in position as it is stuck in, and cannot deflect laterally.

The outside diameter of the cannula point 2.1 basically corresponds to the inside diameter of the shaft tube 2.2 so that only a slight jump in diameter occurs. The shaft tube 2.2 has a very small wall thickness, which is preferably smaller than 0.2 mm. As a result, the flexible cannula 2.0 can even be inserted through curved sections of the cannula guide tube 1.2.

In order to be able to insert the device into the interior of the body smoothly and with no friction, the guide tube 1.2 and the endoscope shaft 1.1 are commonly surrounded by a jacket tube 4, from which the cannula point 2.1 emerges when the handle 5 is operated in the distal direction.

A more proximal section of the coupling 1.8 is provided with an external thread so that the injection cannula can be screwed onto the coupling 1.8 by means of a union nut 2.4 provided with a matching internal thread, and the position of the injection cannula 2.0 in the guide tube 1.2 is fixed.

At the proximal end of the injection cannula 2.0 provided with the Luer connection 2.5, a Luer syringe 6 can be easily connected either filled with the material to be injected or empty for aspiration purposes.

To allow one-handed operation of the device for sticking of the cannula point 2.1 into the body organ, the handle 5 has a handgrip 1.5 rigidly connected to the endoscope shaft 1.1 and a thumb ring 1.7 supported on the block 1.6 so that with one hand the thumb ring together with the block 1.6 can be axially adjusted with respect to the handgrip 1.5.

The perspective representation in FIG. 3 shows the proximal end of the device during insertion of the injection cannula 2.0 through the coupling 1.8 of the cannula guide tube 1.2. The injection cannula 2.0 is inserted into the coupling end of the cannula guide tube 1.2 in such a way that the guide lug 2.3 of the injection cannula 2.0 comes to rest in the groove a of the coupling 1.8. Subsequently, the union nut 2.4 is screwed tightly onto the thread of the coupling 1.8, as a result of which the injection cannula 2.0 is fixed in position in the guide tube 1.2.

FIG. 3 shows additional details of the construction of the handle 5, in particular the mounting of the thumb ring 1.7 on the block 1.6. The thumb ring 1.7 is rigidly connected to a lever bar 5.1 that reaches around the block 1.6 and is supported in a pivoting manner on a link of the block 1.6. At its other end facing away from the thumb ring 1.7, this lever bar 5.1 is linked by means of a spring link 5.2 to a bar 5.3, which is in turn supported in a pivoting but non-moveable manner at the proximal end of the endoscope shaft 1.1 adjacent to the clamping ring 1.9. Thus, when during operation of the device in order to inject collagen and similar materials into a body organ, the thumb grips into the thumb ring 1.7, fingers of the same hand grip the handgrip 1.5 of the handle 5, and the thumb is pressed towards the fingers, the cannula guide tube 1.2 with the inserted injection cannula 2.0 slides in the distal direction on the fixed endoscope shaft 1.1, and the cannula point 2.1 emerges from the distal end of the cannula guide tube 1.2 and can be stuck into the body organ in a play-free and targeted manner.

FIG. 4 illustrates the insertion of an optic 7 into the working element 1.0. The optic 7 is inserted axially into the working element 1.0 in such a way that the pin b comes to rest in the groove c. Following that, the toggle clamp 1.10 is turned from position I to position II in the direction of the arrow S in order to lock the optic 7 in the working element 1.0.

FIG. 5 shows, likewise in a perspective representation, the proximal end of an endoscope being used with the device in accordance with the invention, in which the injection cannula 2.0 and the endoscope optic 7 have already been inserted and locked. FIG. 5 also specifically shows the insertion of the working element with the endoscope optic 7 and the injection cannula 2.0 in the jacket tube 4. The working element 1.0 is inserted axially into the jacket tube 4, which is in situ, in such a way that the positioning pin 1.4 comes to rest in the groove d. In conjunction with this, a toggle clamp e is in position I. For locking, the toggle clamp e is turned in the direction of the arrow T into position II. In conjunction with this, a rinsing tube with a Luer piece can be fastened to the inlet tap 4.1 and connected to an irrigation device. A suction tube with a Luer piece can be fastened to the drain tap 4.2 and connected to a suction pump.

An optical fiber cable can be connected to the optical fiber cable connection 7.1 of the endoscope optic 7 and attached to a light source. Finally, the syringe 6 is attached to the Luer connection of the injection cannula 2.0. Subsequently, the needle (cannula point) is stuck in by operation of the handle 5 in the manner described above, and the injection is carried out.

If in place of the injection cannula 2.0 an insertion tap 3, shown in FIG. 6, is used for examinations through the cannula guide tube, then the coupling is carried out in the same manner as the insertion of the injection cannula was before. Auxiliary instruments such as RF or laser probes, for example, can be connected at the insertion tap 3.

It will be appreciated by those skilled in the art that changes could be made to the embodiments described above without departing from the broad inventive concept thereof. It is understood, therefore, that this invention is not limited to the particular embodiment disclosed, but it is intended to cover modifications within the spirit and scope of the present invention as defined by the appended claims.

I claim:

1. An insertion device for effecting operations comprising:

an endoscope shaft (1.1);

a guide tube (1.2) mounted for axial movement along the endoscope shaft (1.1);

an effector tube (2.0) which is axially adjustable along the endoscope shaft (1.1) located within the guide tube;

a coupling (1.8) located on a proximal end of the guide tube which is connected to a proximal end of the effector tube after the effector tube is inserted into said guide tube (1.2);

a handle (5) having a first handle portion fixed on the endoscope shaft and a second handle portion slidably mounted to the endoscope shaft, the second handle portion being connected to the guide tube (1.2) and the effector tube (2.0), which are together axially adjustable relative to the endoscope shaft (1.1) by movement of the second handle portion relative to the endoscope shaft; and the guide tube (1.2) and the endoscope shaft (1.1) are enclosed by a common jacket tube (4).

2. The device according to claim 1, wherein the endoscope shaft (1.1), the guide tube (1.2) with the coupling (1.8), the effector tube (2.0) and the handle (5) are connected to a proximal block (1.6), the guide tube (1.2) with the effector tube (2.0) being axially adjustable, together with the block (1.6), relative to the endoscope shaft (1.1) by operating the handle (5).

3. The device according to claim 2, wherein the proximal end of the guide tube (1.2) supports the coupling (1.8) and emerges from the block (1.6) on a proximal end at an acute angle to a longitudinal axis of the endoscope shaft.

4. The device according to claim 2, wherein the handle (5) comprises a handgrip (1.5) rigidly connected to the endoscope shaft (1.1) and a thumb ring (1.7) supported by on the block (1.6) in such a way that the thumb ring (1.7) along with the block (1.6) is axially adjustable with respect to the handgrip (1.5) by means of one hand.

5. The device according to claim 1, wherein the effector tube is configured as an injection cannula with a cannula point (2.1) at its distal end, a semi-flexible shaft tube (2.2) as its middle section and a Luer connection (2.5) at its proximal end.

6. The device according to claim 1, wherein a distal end of the guide tube (1.2) is arranged for guiding of a distal end of the effector tube (2.0).

7. The device according to claim 1, wherein the effector tube comprises a cannula for injecting flowable substances into or aspirating flowable substances from human tissue.

8. The device according to claim 1, further comprising an insertion tap (3) removably connected to the coupling (1.8) for inserting auxiliary instruments through the guide tube.

* * * * *